United States Patent [19]

Schön et al.

[11] Patent Number: 5,023,346

[45] Date of Patent: Jun. 11, 1991

[54] PROCESS FOR THE PRODUCTION OF CYCLIC CARBONIC ACID ESTERS

[75] Inventors: Norbert Schön; Hans-Josef Buysch, both of Krefeld, Fed. Rep. of Germany

[73] Assignee: Bayer Aktiengesellschaft, Leverkusen-Bayerwerk, Fed. Rep. of Germany

[21] Appl. No.: 434,443

[22] Filed: Nov. 13, 1989

[30] Foreign Application Priority Data

Nov. 16, 1988 [DE] Fed. Rep. of Germany ....... 3838752

[51] Int. Cl.$^5$ ................. C07D 317/04; C07D 319/02; C07D 323/00
[52] U.S. Cl. .................................. 549/231; 549/228; 549/232; 549/233; 549/234
[58] Field of Search ............... 549/233, 228, 256, 257, 549/231, 232, 234

[56] References Cited

U.S. PATENT DOCUMENTS

| | | | |
|---|---|---|---|
| 3,221,025 | 11/1965 | Prochaska | 549/232 |
| 3,532,715 | 6/1970 | Hostettler | 549/232 |
| 4,501,905 | 2/1985 | Krimm et al. | 549/228 |
| 4,585,566 | 4/1986 | Wollenberg | 549/228 |
| 4,727,134 | 2/1988 | Brunelle et al. | 549/228 |
| 4,767,840 | 8/1988 | Shannon et al. | 549/228 |
| 4,870,127 | 9/1989 | Harris | 549/233 |

FOREIGN PATENT DOCUMENTS

| | | |
|---|---|---|
| 0057360 | 8/1982 | European Pat. Off. . |
| 3502106 | 7/1986 | Fed. Rep. of Germany . |
| 238279 | 10/1987 | Japan ................................. 549/228 |

OTHER PUBLICATIONS

Ludwig and Piech, JACS 73 (1951), 5779.
Sarel et al., J. Org. Chem. 24 (1959), 1873.

*Primary Examiner*—Cecilia Shen
*Attorney, Agent, or Firm*—Connolly & Hutz

[57] ABSTRACT

Cyclic carbonic acid esters are produced by reaction of hydroxy compounds with phosgene in the presence of a heterocyclic compound containing at least one nitrogen atom as ring member in an aromatic ring.

9 Claims, No Drawings

PROCESS FOR THE PRODUCTION OF CYCLIC CARBONIC ACID ESTERS

This invention relates to a process for the production of cyclic carbonic acid esters using catalytic quantities of an N-heterocyclic aromatic compound.

It is known that aliphatic cyclic carbonates can be produced from the basic diols and phosgene with addition of equivalent quantities of a base, preferably an amine base (Houben-Weyl, Methoden der organischen Chemie, 4th Edition, Vol. E 4 (1983), pages 83 et seq.). Whereas 1,2-diols can be converted into the corresponding 5-ring carbonates in high yields in this way, lower yields of the corresponding cyclic carbonates are obtained with 1,3-diols and relatively long-chain $\alpha,\omega$-diols (J. Org. Chem. 24 (1959), 1873). The working-up step of this process is complicated because the amine salts formed generally have to be removed by aqueous extraction (cf. J. Am. Chem. Soc. 73 (1951), 5779; U.S. Pat. No. 3,532,715), which leads to losses of yield, particularly in the case of water-soluble and readily hydrolyzable carbonates. In the same way as aliphatic diols, o,o'-bisphenols can also be reacted with phosgene and equivalent quantities of a nitrogen base to form cyclic carbonic acid esters (U.S. Pat. No. 3,221,025).

Instead of phosgene, carbonic acid esters may also be used for the production of cyclic carbonic acid esters by transesterification (Houben-Weyl, Vol. E 4 (1983), pages 88 et sec.). However, this process involves an additional step because the carbonic acid esters required for the transesterification have to be prepared beforehand, for example from phosgene.

Accordingly, the object of the present invention is to provide a process by which cyclic carbonic acid esters can be obtained in high yields from phosgene and diols without large (substantially equivalent) quantities of bases having to be used and without any need for complicated working-up.

The present invention relates to a process for the production of cyclic carbonic acid esters corresponding to the following formula

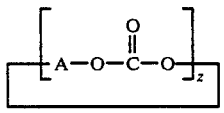
(I)

by reaction of compounds corresponding to the following formula $$HO-A-OH \quad (II)$$

in which
A is a binding link typically encountered in carbonic acid chemistry which is preferably capable of forming monomeric cyclic carbonates, more especially the residue of an aliphatic diol containing 3 to 18 carbon atoms, the residue of a carbocyclic or heterocyclic, non-aromatic diol containing 3 to 8 ring members, the residue of an ether-group-containing aliphatic diol containing up to 5 ether groups and up to 18 carbon atoms or the residue of an aromatic or araliphatic dihydroxy compound containing one or two aromatic nuclei, both OH groups in formula (II) being primary or phenolic OH groups and z in formula (I) is an integer of from 1 to 4 with phosgene, characterized in that the reaction is carried out in the presence of catalytic quantities of a nitrogen-containing compound K in which at least one nitrogen atom is a member of an aromatic ring.

The catalyst K is preferably used in a quantity of from 0.01 to 5% by weight, based on compound II.

Preferred compounds corresponding to formula (II) are, in particular, the following compounds

saturated carbocyclic or heterocyclic compounds corresponding to the following formula

aliphatic compounds containing ether groups corresponding to the following formula

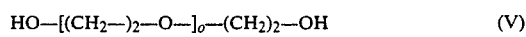

and aromatic or araliphatic compounds corresponding to the following formulae

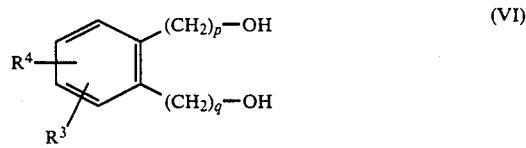
(VI)

and

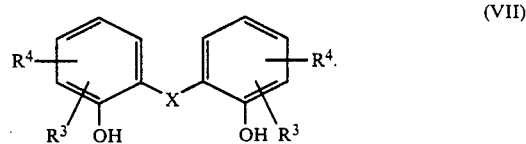
(VII)

In formula (III), the index m is an integer of from 1 to 16.

$R^1$ and $R^2$ independently of one another represent hydrogen, alkyl, more especially $C_1$-$C_6$ alkyl; alkenyl, more especially allyl; aryl, more especially phenyl; aralkyl, more especially benzyl, the radicals mentioned optionally being substituted, or halogen, more especially fluorine, chlorine, bromine or iodine, nitro or OH. Particularly preferred substituents $R^1$ and $R^2$ are $C_1$-$C_6$ alkyl, allyl, phenyl, benzyl, halogen, such as fluorine, chlorine, bromine or iodine, nitro, di($C_1$-$C_4$-alkyl)-amino, hydroxy, hydroxymethyl, $C_1$-$C_4$ alkoxymethyl, allyloxymethyl, halomethyl, a radical corresponding to the following formula

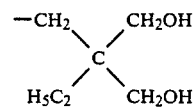

or, together, methylene. The aromatic nuclei mentioned may in turn be substituted by the halogen mentioned, nitro, methyl, ethyl, methoxy or ethoxy.

In formula (IV), Q is a cyclic system containing 3 to 8 and preferably 3 to 6 ring members and may be, for example, a 1,1-bonded cyclopropane, cyclobutane, cyclopentane or cyclohexane ring, a 3,3-bonded oxetane, thietane, thietane-1-oxide, thietane-1,1-dioxide ring or a 1,2-bonded cyclobutane ring.

In formula (V), the index o is an integer of from 1 to 5 and preferably from 1 to 3.

In formula (VI), the indices p and q independently of one another stand for the numbers 0, 1 or 2, the sum of p+q being ≧1. The substituents $R^3$ and $R^4$ independently of one another are hydrogen, $C_1$–$C_6$ alkyl, $C_1$–$C_6$ alkoxy, halogen, such as fluorine, chlorine or bromine, or nitro. $R^3$ and $R^4$ together may even represent a condensed, further aromatic nucleus. In addition, $R^3$ or $R^4$ may also be phenyl.

In formula (VII) X may be a single bond, a binding link, more especially an optionally substituted alkyl radical, particularly methylene and ethylene, a hydrocarbon chain containing 1 to 4 carbon atoms, oxygen, sulfur, —SO— or —$SO_2$—. The substituents $R^3$ and $R^4$ are as defined above.

Examples of compounds corresponding to formula (III) are propane-1,3-diol, pentane-1,5-diol, hexane-1,6-diol, octane-1,8-diol, decane-1,10-diol, dodecane-1,12-diol, octadecane-1,18-diol, 2,2-substituted propane-1,3-diols, such as 2-methylpropane-1,3-diol, 2,2-dimethylpropane-1,3-diol, 2-methyl-2-ethylpropane-1,3-diol, 2-methyl-2-propylpropane-1,3-diol, 2,2-diethylpropane-1,3-diol, 2-t-butyl-2-methylpropane-1,3-diol,2-butyl-2-methylpropane-1,3-diol, 2-allyl-2-methylpropane-1,3-diol, 2,2-diphenylpropane-1,3-diol, 2-methyl-2-phenylpropane-1,3-diol, 2,2-dibenzylpropane-1,3-diol, 2-chloro-2-nitropropane-1,3-diol, glycerol, 2,2,-bis-hydroxymethylpropane-1,3-diol, 2-alloyoxymethyl-2-ethylpropane-1,3-diol (TMP monoallyl ether), 2,2-bis-ethoxymethylpropane-1,3-diol (pentaerythritol diethyl ether), 2,2-bischloromethylpropane-1,3-diol and 2-methylenepropane-1,3-diol.

Examples of compounds corresponding to formula (IV) are cyclopropane-1,1-dimethanol, cyclobutane-1,1-dimethanol, cyclopentane-1,1-dimethanol, 1-cyclohexene-4,4-dimethanol, cyclohexane-1,1-dimethanol, cyclobutane-1,2-dimethanol, 3,3-bishydroxymethyl oxetane and 3,3-bishydroxymethyl thietane.

Examples of compounds corresponding to formulae (V) and (VI) are diethylene glycol, triethylene glycol, o-hydroxymethylphenol and 1,2-bishydroxymethylbenzene.

Suitable bisphenols corresponding to formula (VII) are, for example, optionally substituted 2,2′-dihydroxybiphenyls, optionally substituted bis-(2-hydroxyphenyl)-methanes, such as bis-(2-hydroxy-5-methylphenyl)-methane, bis-(3-tert.-butyl-2-hydroxy-5-methylphenyl)-methane, bis-(5-chloro-2-hydroxyphenyl)-methane, bis-(3,5-dichloro-2-hydroxyphenyl)-methane,bis-(3,5-dimethyl-2-hydroxyphenyl)methane, optionally substituted 2,2-bis-(2-hydroxyphenyl)propanes, such as for example 2,2-bis-(3,5-dimethyl-2-hydroxyphenyl)-propane, and optionally substituted bis-(2-hydroxyphenyl)-oxides and sulfides.

Particularly suitable compounds II for the process according to the invention are those corresponding to the following formula

HO—B—OH                  (VIII)

in which
B is the residue of a propane-1,3-diol, the residue of a polyethylene glycol or the residue of a bisphenol.

Propane-1,3-diols in this context are those corresponding to the following formula

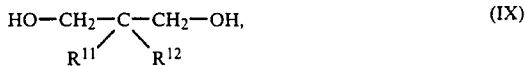
(IX)

in which
$R^{11}$ and $R^{12}$ independently of one another represent hydrogen, $C_1$–$C_4$ alkyl, phenyl, hydroxymethyl, $C_1$–$C_4$ alkoxymethyl or allyloxymethyl or, together, may represent —$CH_2$—O—$CH_2$— or, again together, may represent $C_4$ or $C_5$ alkylidene.

Polyethylene glycols which also fall within the scope of formula (VIII) are those corresponding to the following formula

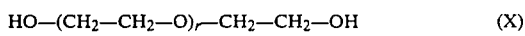
(X)

in which the index r is the number 1 or 2.

The bisphenols also encompassed by formula (VIII) are those corresponding to formula (XI)

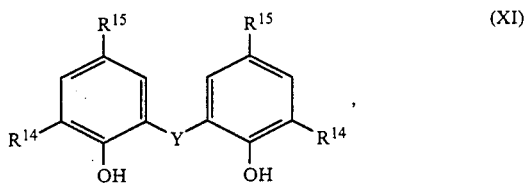
(XI)

in which
Y is a single bond, methylene, oxygen or sulfur and
$R^{14}$ and $R^{15}$ independently of one another represent hydrogen, $C_1$–$C_4$ alkyl or chlorine.

Typical, but by no means exclusive, representatives of the dihydroxy compounds corresponding to formulae (IX), (X) and (XI) are, for example, propane-1,3-diol, 2,2-dimethylpropane-1,3-diol,2-ethyl-2-methylpropane-1,3-diol,2,2-diethylpropane-1,3-diol, 2-methyl-2-propylpropane-1,3-diol, 2-methyl-2-butylpropane-1,3-diol,2-methyl-2-phenylpropane-1,3-diol,2,2-diphenylpropane-1,3-diol, trimethylolalkanes, such as trimethylolpropane and trimethylolethane, trimethylolpropane monopropyl ether, trimethylolpropane monoallyl ether, cyclopentane-1,1-dimethanol, cyclohexane-1,1-dimethanol and 3,3-bis-(hydroxymethyl)-oxetane; diethylene glycol and triethylene glycol; 2,2-dihydroxybiphenyl, bis-(5-methyl-2-hydroxyphenyl)-methane, bis-(3,5-dimethyl-2-hydroxyphenyl)-methane, bis-(5-chloro-2-hydroxyphenyl)methane and bis-(2-hydroxyphenyl)-oxide.

The process according to the invention is carried out in the presence of from 0.01 to 5% by weight and preferably in the presence of from 0.1 to 2% by weight, based on the dihydroxy compound, of a compound K. The compounds K are above all, nitrogen bases which carry the nitrogen atom in a aromatic 5- or 6-membered ring and, in addition, bear no functional groups which enter into firm bonds with phosgene, chlorocarbonic acid esters or carbonates under the reaction conditions, such as for example amino, hydroxy or mercapto groups. In addition to the nitrogen atom, other heteroatoms may be present in the ring system, including for example oxygen, sulfur or further N atoms. In addition, the heterocycle may be condensed with other aromatic heterocycles or even with aromatic carbocycles.

Examples of the compounds K are pyridine, quinoline, isoquinoline; picolines, pyrazine, pyridazine and benzocondensed derivatives thereof; triazines, such as 2,4,6-trimethyl triazine, pyrazole, imidazole, triazole and thiazole and also the compounds substituted by $C_1-C_4$ alkyl, $C_1-C_4$ alkoxy, $C_1-C_4$ carbalkoxy or halogens such as 2-methyl imidazole, and also benzocondensed derivatives thereof, such as benzimidazole, benztriazole or benzthiazole. The condensed benzene nuclei in systems such as these may in turn be substituted by $C_1-C_4$ alkyl, $C_1-C_4$ alkoxy, $C_1-C_4$ carbalkoxy, halogen or nitro.

Preferred compounds K for the process according to the invention are quinolines, picolines, benzimidazoles, pyrazoles, triazoles and benztriazoles, pyridines and imidazoles and especially picolines, pyridine and imidazole. Several of these compounds may of course also be used in the form of a mixture. In addition, instead of the free bases of these compounds, it is possible to use salts thereof, for example hydrochlorides, hydrobromides, sulfates, etc. It is also possible to use salts from which the hydrochlorides may readily form in the reaction mixture, for example the formates, acetates, phosphates, carbamates, picrates and others.

The reaction of the dihydroxy compound with phosgene may be carried out in the melt of the dihydroxy compound or in solution, for which purpose inert solvents, such as hydrocarbons, halogenated hydrocarbons, esters, nitriles, ethers, amides, etc., may be used. Examples of such solvents are dichloromethane, chloroform, toluene, xylene, chlorobenzene, dichlorobenzene, trimethylbenzene, diphenyl ether, chloronaphthalene, butyl acetate, benzonitrile, dimethyl acetaxide, N-methyl pyrrolidone.

The quantity of solvent used, if any, is not critical to the process according to the invention and may therefore vary within wide limits. For example, it is possible to use from 20 to 2,000% by weight and preferably from 100 to 1,000% by weight of solvent, based on the weight of the dihydroxy compound used.

Phosgene is generally used in a quantity 0.8 to 2 mol, preferably in a quantity of from 0.9 to 1.5 mol and more preferably in a quantity of from 0.9 to 1.1 mol per mol of the compound corresponding to formula (II) for the reaction according to the invention; the components may even be subsequently added. The phosgene may be initially introduced in the solvent used, if any, or may even be added in the form of a solution to the (dissolved or suspended) dihydroxy compound initially introduced. Finally, the phosgene may be condensed into the solution, suspension or melt of the dihydroxy compound in liquid or gaseous form without any more solvent. The N-heterocyclic aromatic compound to be used in accordance with the invention may be initially introduced together with the starting material or may even be added after the phosgene.

The reaction according to the invention is carried out at a temperature in the range from $-20°$ C. to $+300°$ C. and preferably at a temperature in the range from $120°$ to $250°$ C. in the case of aromatic compounds and at a temperature of from $-20°$ to $140°$ C. in the case of aliphatic compounds. The reaction may be carried out by increasing the temperature within the limits indicated in the course of the reaction. Where a solvent is used, it may be distilled off during the increase in temperature. During the reaction according to the invention, it is possible to change from a relatively low-boiling solvent to a relatively high-boiling solvent This can be done very easily by distilling off the low-boiling solvent during the increase in temperature and, at the same time, introducing the higher-boiling solvent into the reaction mixture either continuously or in batches. The reaction is then completed in the higher boiling solvent or, where all the solvents used are completely distilled off, even in a melt of the cyclic carbonic acid ester produced. In the reaction of aliphatic dihydroxy compounds or aliphatic dihydroxy compounds containing ether groups or cyclic dihydroxy compounds containing non-aromatic groups, it has proved to be of advantage to apply a temperature in the range from $-20°$ C. to $+140°$ C. and preferably in the range from $-5°$ C. to $+120°$ C. It is of particular advantage in this regard to begin the reaction at a temperature in the range from $-5°$ C. to $+50°$ C. and preferably in a temperature in the range from $-5°$ C. to $+15°$ C. In this variant also, the temperature may be increased during the reaction in the described manner.

The reaction according to the invention is over when there is no further evolution of hydrogen chloride, even in the event of an increase in temperature. To remove residues of hydrogen chloride, it may be advisable either to apply a vacuum or to pass a stream of inert gas (for example nitrogen) through the reaction mixture.

The cyclic carbonic acid esters may be isolated from the reaction mixture by standard methods, for example by crystallization or distillation; in the case of high-boiling reaction products, vacuum distillation or high vacuum distillation may also be considered.

The yields of cyclic carbonic acid esters are generally very high. In the case of 6-membered, aliphatic compounds they are generally higher than 90% of the theoretical yield. The crude products are generally pure enough for many applications.

The cyclic carbonic acid esters obtainable in accordance with the invention are valuable starting materials for homo- and copolycarbonates, duromer systems (EP-A 188 204) and copolymers of cyclic carbonic acid esters and lactams (DE-A 30 40 612).

EXAMPLE 1

5,5-dimethyl-1,3-dioxan-2-one 198 g (2.00 mol) phosgene were introduced over a period of 1,5 h at 0° to 5° C. into a suspension of 208 g (2.00 mol) 2,2-dimethylpropane-1,3-diol and 600 ml dry dichloromethane, followed by stirring at that temperature until the initially vigorous evolution of hydrogen chloride had abated. The discharge of phosgene was prevented by an effective reflux condenser (dry ice). The solvent was then removed in vacuo, 500 mg (0.2% by weight) imidazole and 500 ml toluene were added and the reaction was completed by slowly increasing the temperature to 110° C. until the evolution of hydrogen chloride had stopped (3 hours). Residues of hydrogen chloride were then removed by application of a low vacuum. Removal of the toluene and fractionation of the residue in vacuo left 121 g (93%) of a solid product (boiling point 142° to 146° C./10 mbar). Recrystallization from ethyl acetate gave 117 g (90%) of product (Mp. 108° to 109° C.). Further working up is unnecessary.

EXAMPLE 2

Cyclic carbonate of 2,2'-dihydroxybiphenyl 150 g (1.50 mol) phosgene were introduced over a period of 2.5 h at 115° to 120° C. into a solution of 186 g (1.00 mol) 2,2'-dihydroxybiphenyl and 1.00 g imidazole. To complete the evolution of hydrogen chloride, the solution was heated for 2 hours until a reflux began, after which the solvent was distilled off in vacuo. The solid residue (212 g) was distilled in a high vacuum. A colorless, crystallizing distillate (Bp. 126° to 130° C./0.35 to 0.5 mbar) was obtained in a yield of 189 g (89%). Mp.: 99° to 100° C. (from diisopropyl ether); IR: 1805 cm$^{-1}$ (C=O).

Further working up is unnecessary.

We claim:

1. A process for the production of cyclic carbonic acid esters corresponding to formula I

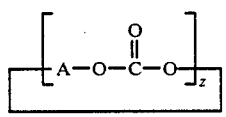 (I)

by reaction of compounds corresponding to formula II

in which z is an integer of from 1 to 5 and

A is a binding link selected from the residue of an aliphatic diol containing 3 to 18 carbon atoms, the residue of a non-aromatic, carbocyclic or heterocyclic diol containing 3 to 8 ring members, the residue of an ether-group-containing aliphatic diol containing up to 5 ether groups and up to 18 carbon atoms, and the residue of an aromatic or araliphatic dihydroxy compound containing one or two aromatic nuclei with phosgene, wherein the reaction is carried out in the presence of 0.01 to 5% by weight, based on the weight of the compound of formula II, of a catalytic compound which contains at least one nitrogen atom as a member of an aromatic ring system.

2. A process as claimed in claim 1, wherein compound II has the following structure

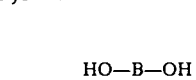

in which

B is the residue of a propane-1,3-diol, the residue of a polyethylene glycol or the residue of a bisphenol which remains after the removal of two OH groups.

3. A process as claimed in claim 1, wherein the catalytic compound is used in a quantity of from 0.1 to 2% by weight, based on compound II.

4. A process as claimed in claim 1 wherein the catalytic compound is selected from a pyridine, quinoline, picoline, imidazole, benzimidazole, pyrazole, triazole or benzotriazole.

5. A process as claimed in claim 1, wherein the reaction is carried out in the presence of an inert solvent.

6. A process as claimed in claim 1, wherein from 0.8 to 2 mol phosgene are used per mol of compound corresponding to formula (II).

7. A process as claimed in claim 1, wherein the temperature is increased during the reaction and, where a solvent is used, the solvent is distilled off, the solvent distilled off being replaced by a solvent of higher boiling point during the increase in temperature and the reaction being completed in the solvent of higher boiling point or, where all solvents are completely distilled off, in the melt of the reaction product.

8. A process as claimed in claim 1, wherein compound II is an aromatic compound and the reaction is carried out at a temperature in the range from 120° to 250° C.

9. In a process for preparing a cyclic carbonic acid ester by reacting a diol with phosgene, the improvement comprising carrying out the reaction in the presence of 0.01 to 5% by weight, based on the weight of diol, of a catalytic compound selected from a pyridine, quinoline, picoline, imidazole, benzimidazole, pyrazole, triazole, or a benzotriazole.

* * * * *